United States Patent
Higuchi et al.

(10) Patent No.: US 9,046,518 B2
(45) Date of Patent: Jun. 2, 2015

(54) DETECTOR AND DETECTION METHOD

(75) Inventors: Masayuki Higuchi, Hitachi (JP);
Yuuichi Nakano, Hitachi (JP); Nahoko Suzuki, Hitachi (JP); Miki Tanimoto, Hitachi (JP); Kouhei Yamashita, Hitachi (JP)

(73) Assignee: Hitachi Chemical Company, Ltd., Tokyo (JP)

( * ) Notice: Subject to any disclaimer, the term of this patent is extended or adjusted under 35 U.S.C. 154(b) by 0 days.

(21) Appl. No.: 13/263,362

(22) PCT Filed: Apr. 9, 2009

(86) PCT No.: PCT/JP2009/057269
§ 371 (c)(1),
(2), (4) Date: Dec. 8, 2011

(87) PCT Pub. No.: WO2010/116507
PCT Pub. Date: Oct. 14, 2010

(65) Prior Publication Data
US 2012/0095308 A1   Apr. 19, 2012

(51) Int. Cl.
*A61B 5/00* (2006.01)
*G01N 33/558* (2006.01)
*G01N 33/68* (2006.01)

(52) U.S. Cl.
CPC .......... *G01N 33/558* (2013.01); *G01N 33/6854* (2013.01)

(58) Field of Classification Search
CPC . Y10S 435/97; Y10S 436/81; Y10S 435/805; Y10S 435/81; Y10S 436/805; Y10S 436/806; Y10S 436/807; Y10S 436/814; Y10S 436/815; Y10S 436/823; Y10S 436/829; G01N 33/558; G01N 33/521; G01N 33/543
USPC ........ 422/412; 436/514, 534; 435/287.2, 6.16
See application file for complete search history.

(56) References Cited

U.S. PATENT DOCUMENTS 5,789,154 A * 8/1998 Durst et al. .................. 435/6.16
6,399,398 B1 * 6/2002 Cunningham et al. ........ 436/534
(Continued)

FOREIGN PATENT DOCUMENTS

| CA | 2199823 | 3/1998 |
| CN | 201004063 Y | 1/2008 |

(Continued)

OTHER PUBLICATIONS

CA Office Action Appln. No. 2,758,152 dated Nov. 19, 2012 in English.
(Continued)

*Primary Examiner* — Sally Merkling
(74) *Attorney, Agent, or Firm* — Fitch, Even, Tabin & Flannery

(57) ABSTRACT

Provided is a strip-shaped detector that detects an analyte in a liquid sample. The detector includes a collecting member that directly collects a liquid sample from a living organism, a holding member that holds a labeling reagent binding specifically to the analyte in a state where the labeling reagent can move along with the movement of the liquid sample, a detecting member to which a detection reagent is immobilized which captures a complex of the analyte and the labeling reagent by binding specifically to the analyte, an absorbing member that can absorb the liquid sample, and a liquid-impermeable supporting member, wherein the respective members are arranged on the supporting member in the longitudinal direction of the detector so that the liquid sample moves through the inside of these members, and the collecting member includes a protruding portion sticking out of the supporting member at the upstream side in the movement direction of the liquid sample.

29 Claims, 9 Drawing Sheets

(56) References Cited

U.S. PATENT DOCUMENTS

| | | | |
|---|---|---|---|
| 2003/0017615 A1* | 1/2003 | Sidwell et al. | 436/514 |
| 2005/0175992 A1 | 8/2005 | Aberl | |
| 2009/0004058 A1 | 1/2009 | Liang et al. | |

FOREIGN PATENT DOCUMENTS

| | | | | |
|---|---|---|---|---|
| CN | 101169413 A | | 4/2008 | |
| CN | 101329338 A | | 12/2008 | |
| CN | 101393213 A | | 3/2009 | |
| EP | 0 782 707 B1 | | 7/1997 | |
| JP | 63-061953 | | 3/1988 | |
| JP | 08-166379 | | 6/1996 | |
| JP | 2919392 | | 7/1997 | |
| JP | 10-505909 | | 6/1998 | |
| JP | 10-332700 | | 12/1998 | |
| JP | 2890384 | | 2/1999 | |
| JP | 2001-013141 | | 1/2001 | |
| JP | 2001-228151 | | 8/2001 | |
| JP | 2003-121445 | | 4/2003 | |
| JP | 2004-536309 | | 12/2004 | |
| JP | 2005-529305 | | 9/2005 | |
| JP | 2006-501456 | | 1/2006 | |
| JP | 2006-029830 | | 2/2006 | |
| JP | 2006-153523 | * | 6/2006 | G01N 33/543 |
| JP | 2006-194785 | | 7/2006 | |
| JP | 2008-164300 | * | 7/2008 | G01N 33/543 |
| JP | 2009-085839 | | 4/2009 | |
| TW | 200302349 | | 8/2003 | |
| TW | I224673 | | 12/2004 | |
| TW | I224673 | | 12/2004 | |
| TW | 200609506 | | 3/2006 | |
| WO | WO 96/09546 | | 3/1996 | |
| WO | WO 97/23773 | | 7/1997 | |
| WO | WO 00/70327 | | 11/2000 | |
| WO | WO 01/36964 | | 5/2001 | |
| WO | WO 2006/073500 A2 | | 7/2006 | |
| WO | WO 2006/102697 | | 10/2006 | |
| WO | WO 2007/082545 A1 | | 7/2007 | |
| WO | WO 2008/075213 A2 | | 6/2008 | |

OTHER PUBLICATIONS

JP office action of Appln. No. 2007-257892 dated Oct. 16, 2012.
JP Office Action of Appln. 2007-257892 dated Jan. 17, 2012.
TW Office Action of Appln. No. 098112228 dated Jun. 11, 2014.
CN Office Action of Appln. No. 200980158546.7 dated Apr. 11, 2014.
Office Action of SG Appln. No. 201107340-0 dated Oct. 1, 2013 in English.
Office Action of CN Appln. No. 200980158546.7 dated Sep. 10, 2013.
Andrea Leonard!, In-Vivo Diagnostic Measurements of Ocular Inflammation, Current Opinion in Allergy and Clinical Immunology, vol. 5, No. 5, Oct. 1, 2005, XP009147444, pp. 464-472.
EP Search Report of Appln. No. 09843017.6 dated Mar. 8, 2013 in English.
International Search Report of International Appl. PCT/JP2009/057269 dated May 19, 2009 in English.
International Preliminary Report on Patentability of International Appl. PCT/JP2009/057269 dated Nov. 24, 2011 in English.
JP Office Action of Appln. 2007-257881 dated Dec. 13, 2011.

* cited by examiner

Fig. 9

[Table 2]

| Type of fibrous substrate | | | Diameter (mm) | | Picture of spot |
|---|---|---|---|---|---|
| | | | 1 | 2 | |
| (A) | Unwoven wood pulp fabric | No mixing | 3.5 | 3.5 | |
| (B) | | Mixed with rayon | 3.5 | 3.5 | |
| (C) | | | 3.0 | 3.0 | |
| (D) | | Mixed with synthetic fiber | 4.0 | 4.0 | |
| (E) | | | 3.0 | 3.0 | |
| (F) | Filter paper | | 11.0 | 11.0 | |
| (G) | Hydroxy polyester | | 4.0 | 4.0 | |
| (H) | Glass fiber | | 4.0 | 3.5 | |

DETECTOR AND DETECTION METHOD

TECHNICAL FIELD

The present invention relates to a detector and a detection method.

BACKGROUND ART

As a strip-shaped detector that detects an analyte in a liquid sample originated from a living organism, detectors disclosed in patent literature 1 to 3 are known, for example. Generally, in order to detect the analyte in the liquid sample originated from a living organism, it is necessary to perform a complicated operation that includes a plurality of steps such as collecting a liquid sample from the living organism, treating the collected liquid sample with a predetermined procedure such as dilution, extraction, or the like, and then applying the sample to the above-described detector.

Accordingly, as means for simplifying these steps, a detector that directly collects a sample from a living organism is proposed in the disclosure of patent literature 4, for example.

CITATION LIST

Patent Literature

Patent literature 1: Japanese Patent No. 2919392
Patent literature 2: Japanese Patent No. 2890384
Patent literature 3: Japanese Unexamined Patent Application Publication No. 2003-121445
Patent literature 4: PCT Japanese Translation Patent

SUMMARY OF INVENTION

Technical Problem

However, when a liquid sample is directly collected from a living organism, the living organism feels pain in some cases since the detector contacts the living organism. Moreover, in order to collect a large amount of a liquid sample, the detector needs to be brought into contact with the living organism for a long time, which imposes a great burden on the living organism. On the other hand, if the time of the contact between the living organism and the detector is shortened to reduce the burden on the living organism, it is difficult to obtain a sufficient amount of the liquid sample. As a result, measured values show variations, and sufficient detection results cannot be obtained. In this way, direct collection of the liquid sample from a living organism in the related art has a problem in that great burden is imposed on the living organism, the amount of the sample collected is small, and detection sensitivity is low.

Although patent literature 4 makes a mention regarding a material of a portion that collects the liquid sample, a specific configuration for resolving the above problems is not sufficiently disclosed in the patent literature.

In this respect, the invention aims to provide a detector and a detection method in which sufficient detection results can be obtained by direct collection of the liquid sample from a living organism, and burden imposed on the living organism can be reduced.

Solution to Problem

That is, the invention, is a strip-shaped detector detecting an analyte in a liquid sample. The detector includes a collecting member directly collecting a liquid sample from a living organism, a holding member including a labeling reagent binding specifically to the analyte, the labeling reagent being held in a state where the labeling reagent can move along with the movement of the liquid sample, a detecting member including a detection reagent capturing a complex of the analyte and the labeling reagent by binding specifically to the analyte, and the detection reagent being immobilized, an absorbing member being capable of absorbing the liquid sample, and a liquid-impermeable supporting member, wherein the collecting member, the holding member, the detecting member, and the absorbing member are arranged on the supporting member in the longitudinal direction of the detector so that the liquid sample moves through the inside of these members in the above order of the members by capillarity, and the collecting member includes a protruding portion sticking out of the supporting member at the upstream side in the movement direction of the liquid sample.

In the detector according to the invention, the collecting member that directly collects the liquid sample from a living organism includes the protruding portion sticking out of the supporting member. As a result, when the collecting member is brought into contact with a sample collecting site of the living organism, it is possible to bring only the protruding portion into contact with the site, and to prevent other members such as the supporting member and the like from contacting the site. Consequently, it is possible to sufficiently reduce the pain that the living organism feels and the damage to the health of the living organism caused by the contact with respective reagents. In addition, since the protruding portion includes a flat surface, the pain is further reduced. In addition, since the detector includes the liquid-impermeable supporting member, it is possible to sufficiently prevent the collected liquid sample from leaking from the rear surface of the collecting member, the holding member, and the detecting member. It is preferable that the liquid-impermeable supporting member be provided under the detecting member and the absorbing member from the viewpoint of preventing the liquid sample from leaking from the rear surface. Furthermore, it is preferable that the supporting member be also provided at the downstream side of the holding member from the viewpoint of preventing the reflux of the liquid sample. With this configuration, it is possible to detect the analyte even if the amount of the liquid sample is small. Accordingly, it is possible to shorten a time when the collecting member contacts the sample collecting site. Employing this configuration makes it possible for the detector to obtain sufficient detection results by directly collecting the liquid sample from the living organism, and the burden imposed on the living organism can be reduced. The detector of the invention can be suitably used as a chromatography detector that detects an analyte in the liquid sample, for example, as a chromatography detector that directly collects the liquid sample such as tears from the living organism.

The holding member may include a portion overlapped with a portion of the detecting member, and the length along the longitudinal direction of the overlapped portion is preferably equal to or longer than the length along the longitudinal direction of a portion holding the labeling reagent in the holding member, and more preferably longer than the length along the longitudinal direction of the portion holding the labeling reagent. In this manner, since a contact area between the holding member and the detecting member increases, the liquid sample easily moves to the detecting member from the holding member by capillarity, and a detection time is reduced. Therefore, the burden imposed on the living organism such as a patient with a dry eye syndrome or the like is reduced. In this case, those members are more preferably overlapped with each other such that the holding member becomes the top. In this manner, since capillary flow in a vertical direction is created in the overlapped portion, the liquid sample more easily moves to the detecting member from the holding member by capillarity. When a portion of the holding member and a portion of the detecting member are overlapped with each other, the liquid-impermeable supporting member is preferably provided under the overlapped portion, and more preferably provided to at least 5 mm at the upstream side of the overlapped portion. In this manner, leakage of the liquid sample is further effectively suppressed.

It is preferable that the collecting member and the holding member share a single fibrous substrate. In this case, the labeling reagent is held in the end portion of the downstream side in the movement direction of the fibrous substrate so as to form the holding member. In this manner, integrating the collecting member and the holding member and using a single fibrous substrate simplify the configuration of the detector. As a result, it is possible to reduce production steps and costs, and the liquid sample more easily moves to the holding member from the collecting member by capillarity.

In the detector in which, the collecting member and the holding member share a single fibrous substrate as described above, the fibrous substrate may include a portion overlapped with a portion of the detecting member. The length along the longitudinal direction of the overlapped portion is preferably equal to or longer than the length along the longitudinal direction of the portion that holds the labeling reagent in the fibrous substrate, and more preferably longer than the length along the longitudinal direction of a portion that holds the labeling reagent. In this manner, since a contact area between the fibrous substrate and the detecting member increases, the liquid sample easily moves to the detecting member from the fibrous substrate by capillarity, and the movement speed of the liquid sample increases. Therefore, a detection time is reduced, and the burden imposed on the living organism such as a patient with a dry eye syndrome or the like is reduced. In this case, it is preferable that the fibrous substrate be overlapped with the top of the detecting member. In this manner, since capillary flow in a vertical direction is created in the overlapped portion, the liquid sample more easily moves to the detecting member from the fibrous substrate by capillarity.

The collecting member and the fibrous substrate are preferably unwoven fabric including pulp. The unwoven fabric including pulp has an ability to retain a large amount of water per unit mass, that is, has a high water retentivity. Accordingly, even when the amount of the analyte that is included in the liquid sample is minute, it is possible to improve the detection sensitivity by increasing the amount of the liquid sample collected. In addition, being a soft material, the unwoven fabric including pulp is also desirable in the respect that the unwoven fabric does not easily cause pain when brought into contact with the living organism.

In the unwoven fabric including pulp, the liquid sample is not easily diffused. Accordingly, the use of the unwoven fabric as the collecting member makes it possible to improve the detection sensitivity of the analyte. Particularly, when the unwoven fabric including pulp is used as the single fibrous substrate that the collecting member and the holding member share, there is also an advantage that the labeling reagent held in the end portion of the downstream side of the fibrous substrate is held near the end portion without touching the living organism when the liquid sample is directly collected from the living organism. Accordingly, the unwoven fabric including pulp is suitably used as the fibrous substrate in the detector in which, the collecting member and the holding member are integrated. Due to the advantage, the unwoven fabric including pulp is suitable as a collecting member for a chromatography detector that can sufficiently reduce the burden imposed on the living organism when the liquid sample is directly collected from the living organism.

The pulp is preferably wood pulp. The wood pulp has a superior water retentivity. Therefore, the use of the wood pulp makes it easy to obtain an effect of improving the detection sensitivity.

To the unwoven fabric including pulp, rayon and/or synthetic fiber may be further mixed. Mixing these materials to the unwoven fabric improves the strength, surface smoothness, and flexibility of the unwoven fabric. Particularly, the unwoven fabric mixed with the synthetic fiber is preferable in terms of an excellent water-absorbing rate.

The unwoven fabric is preferably compressed unwoven fabric. Specifically, the density of the unwoven fabric is preferably 40 mg/cm$^3$ or more, and more preferably 45 mg/cm$^3$ or more, still more preferably 50 mg/cm$^3$ or more, even more preferably 55 mg/cm$^3$ or more, and much more preferably 60 mg/cm$^3$ or more. The thickness of the unwoven, fabric is preferably 0.8 mm or less, more preferably 0.75 mm or less, still more preferably 0.7 mm or less, and even more preferably 0.65 mm or less.

The unwoven fabric may be obtained by compressing a normal unwoven fabric including pulp by 10% or more. That is, the normal unwoven fabric including pulp is compressed at a compression rate of 10% or higher, whereby the unwoven fabric with a thickness of 90% or less is obtained. Preferably, by compressing normal unwoven fabric including pulp by 20% or more, that is, by compressing the normal unwoven fabric until the thickness becomes 80% or less, the unwoven fabric described above is obtained. More preferably, by compressing the normal unwoven fabric including pulp by 30% or more, that is, by compressing the normal unwoven fabric until the thickness becomes 70% or less, the unwoven fabric described above is obtained.

The maximum width of the collecting member, the holding member, and the detecting member in a direction orthogonal to the longitudinal direction is preferably 0.8 ram to 3 mm. If the width is larger than 3 mm, the amount of liquid sample necessary for detection increases, hence a sufficient amount of the liquid sample tends not to be obtained. On the other hand, if the width is smaller than 0.8 mm, there is a tendency that it is difficult to confirm the color development upon capture caused by the labeling reagent on the detecting member.

It is preferable that the detecting member further include a control reagent binding specifically to the labeling reagent. The control reagent is immobilized to the downstream side from the detection reagent. The control reagent binds to the labeling reagent that has moved along with the movement of the liquid sample at the downstream side from the detection reagent, whereby it is possible to confirm that a sufficient amount of the liquid sample for detection has been collected.

It is preferable that a portion of the detecting member be overlapped with a portion of the absorbing member. It does not matter which one will be the top between the portions of the detecting member and the portion of the absorbing member when they are overlapped with each other. However, it is preferable that the absorbing member be the top when they are overlapped with each other. When a portion of the detecting member and a portion of the absorbing member are overlapped with each other, the liquid-impermeable supporting member is preferably provided under the overlapped portion, more preferably provided to at least 5 mm of the downstream side of the overlapped portion, and still more preferably provided to at least 10 mm of the downstream side.

The length of the protruding portion is preferably 5 mm or more. If the length of the protruding portion is less than 5 mm, members other than the collecting member of the detector easily touch the living organism when the liquid sample is collected from the living organism, which leads to a possibility that pain may be given to the living organism. Particularly, when the liquid sample is tears, the protruding portion is inserted in the inferior conjunctival fornix of the living organism and folded at outer edge of the lower eyelid, and the tears are collected while the detector is hung in a vertical direction. At this time, the protruding portion needs to have a sufficient length.

It is preferable that the detector further include a first adhesive member. The first adhesive member adheres to the surfaces of the end portion of the downstream side of the collecting member; the holding member; and the end portion of the upstream side of the detecting member, the surfaces being at the opposite side of the these members from supporting member, and includes a non-adhesive face at the opposite side from the adhesive face.

By adhering to the collecting member, the holding member, and the detecting member, the first adhesive member can prevent these members from being peeled of from each other and improve the strength of the detector. In addition, by covering the surface of these members, the first adhesive member can prevent the liquid sample from volatilizing from these members and obtain sufficient detection results with smaller amount of sample collected. Moreover, by covering the members as if pressing the members from the top, the first adhesive member promotes the movement of the liquid sample caused by capillarity.

It is preferable that the detector further include a second adhesive member. The second adhesive member adheres to the end portion of the downstream side of the detecting member, the absorbing member, and the end portion of the downstream side of the supporting member while wrapping these members. The second adhesive member may include a non-adhesive face at the opposite side from the adhesive face adhering to the respective members. It is preferable that a portion for pick up be formed at the end portion of the downstream side in the second adhesive member, in a manner in which the second adhesive members adhere to each other in a portion where the second adhesive member is folded back.

By adhering to the detecting member, the absorbing member and the supporting member, the second adhesive member can prevent these members from being peeled off from each other and improve the strength of the detector. Particularly, by adhering to these members as if covering these members from the downstream side of the members, the second adhesive member can effectively reinforce the structure of the detector. In addition, since the second adhesive member covers the surface of the absorbing member, and the outer surface (surface of the opposite side from the adhesive face) thereof is non-adhesive, there is also an advantage that a user who uses the detector by gripping the end portion of the downstream side of the detector with his or her hand does not contaminate the hand. Particularly, when the user holds the portion for pick up to use the detector, reagents or the like are less likely to contact the user's hand, so the user can safely use the detector. That is, the second adhesive member functions as a holding portion of the detector.

It is preferable that the supporting member include a first supporter also serving as a lining of the detecting member, and a second supporter provided on the opposite side of the first supporter from the detecting member. In this manner, the supporting member includes a plurality of supporters, whereby the structure of the detector is further reinforced, and an effect of preventing the leakage or volatilization of the liquid sample from the detecting member or the like also improves.

It is preferable that the second supporter be separated in the longitudinal direction on the first supporter. Due to the separation of the second supporter, it is possible to easily adjust the length of the detector by changing an arrangement pattern of the second supporter, and variation in production is obtained. If the second supporter is separated in a portion other than on the first supporter, the liquid sample easily leaks outside the detector. The second supporter is preferably provided under the absorbing member from the viewpoint of preventing the leakage of the liquid sample from the rear surface, and more preferably provided at the downstream side of the holding member from the viewpoint of preventing the reflux of the liquid sample in addition to prevention of the leakage from the rear surface. When a portion of the holding member and a portion of the detecting member are overlapped with each other, the second supporter is preferably provided under the overlapped portion, and more preferably provided to at least 5 mm of the upstream side of the overlapped portion. When a portion of the detecting member and a portion of the absorbing member are overlapped with each other, it is necessary for the second supporter to be provided under the overlapped portion, and the second supporter is preferably provided to at least 5 mm of the downstream side of the overlapped portion, and more preferably provided to at least 10 mm of the downstream side. In this manner, the leakage of the liquid sample is further effectively suppressed.

It is preferable that the supporting member have a function of highlighting the color development upon capture caused by the labeling reagent. In this manner, it is easy to confirm the color development upon capture on the detecting member, and the analyte can be easily detected.

When the supporting member does not have the function described above, it is preferable that the detector further include a background member having a function of highlighting the color development upon capture caused by the labeling reagent, the background member being provided on the opposite side of the supporting member from the detecting member. In this manner, if the background member is provided, it is easy to confirm the color development upon capture on the detecting member, and the analyte can be easily detected. The color development upon capture refers to color development (detection line) that can be confirmed when the label of the labeling reagent binding to (capturing) the analyte or the control reagent develops a color in a detection reagent-immobilizing portion or a control reagent-immobilizing portion. From a viewpoint of highlighting the color development upon capture, if the background member is white, the detection line is easily confirmed, which is thus more preferable.

It is preferable that the background member be a paper tape having an adhesive face on the opposite side of the supporting member from the detecting member. If the background member is a paper tape, it is possible to easily put a mark showing a position, where the detection reagent or the control reagent is immobilized, on the surface of the background member side opposite from the supporting member through coloring or the like. When the supporting member includes a plurality of supporters, the background member makes the supporters adhere to each other, whereby the detector can be reinforced.

When the background member is made with paper, it is preferable that the supporting member extend 2 mm or more toward the upstream side from the background member. If the supporting member extends not longer than the background member, or if the extending portion is less than 2 mm, the liquid sample in the collecting member is likely to permeate the background member. If the liquid sample permeates the background member, a background tends to rise or the detector tends to twist which leads to a tendency that it is difficult to confirm the color development upon capture. In addition, if the liquid sample permeates the background member from the collecting member, the amount of the liquid sample that moves to the bolding member or the detecting member decreases accordingly. Therefore, sensitivity is reduced, and sufficient detection results tend not to be obtained.

The mass of the detector is preferably 0.8 g or less. If the mass is more than 0.8 g, for example, when the liquid sample is tears, and the detector is hung in a vertical direction from the inferior conjunctival fornix of the living organism to collect the tears, the detector falls due to its own weight.

The detector is particularly useful when the living organism is a human being and the liquid sample is tears. Generally, collecting tears imposes a great burden on a subject. Particularly, when the subject suffers from a dry eye syndrome, there is a tendency that the subject suffers from pain, and that only an extremely small amount of tears, such as less than 10 μL, is collected. However, if the detector described above is used, it is possible to collect tears without imposing an excessive burden on such a subject, and sufficient detection results can be obtained even if the amount of tears collected is less than 10 μL.

In addition, the detector is particularly useful when the analyte is an IgE antibody. In this case, the labeling reagent is obtained by labeling an antibody recognizing the IgE antibody as an antigen with a labeling substance, the detection reagent is an antibody recognizing the IgE antibody as an antigen and including a recognition site different from that of the antibody included in the labeling reagent, and the control reagent is an antibody recognizing the antibody included in the labeling reagent as an antigen. By detecting the IgE antibody in the liquid sample originated from the living organism by means of the detector, it is possible to easily determine whether or not the living organism suffers from an allergy such as pollenosis.

As another aspect, the invention relates to a detection method that detects the analyte in the liquid sample by using the detector.

According to the detection method, it is possible to obtain sufficient detection results by directly collecting the liquid sample from the living organism without imposing an excessive burden on the living organism.

Advantageous Effects of Invention

According to the invention, it is possible to provide a detector and a detection method in which sufficient detection results can be obtained by direct collection of a liquid sample from a living organism, and burden imposed on the living organism can be reduced.

BRIEF DESCRIPTION OF DRAWINGS

FIG. 9 is a table (TABLE 2) showing labeling reagent holding ability of eight types of fibrous substrates.

DESCRIPTION OF EMBODIMENT

Figure 1:
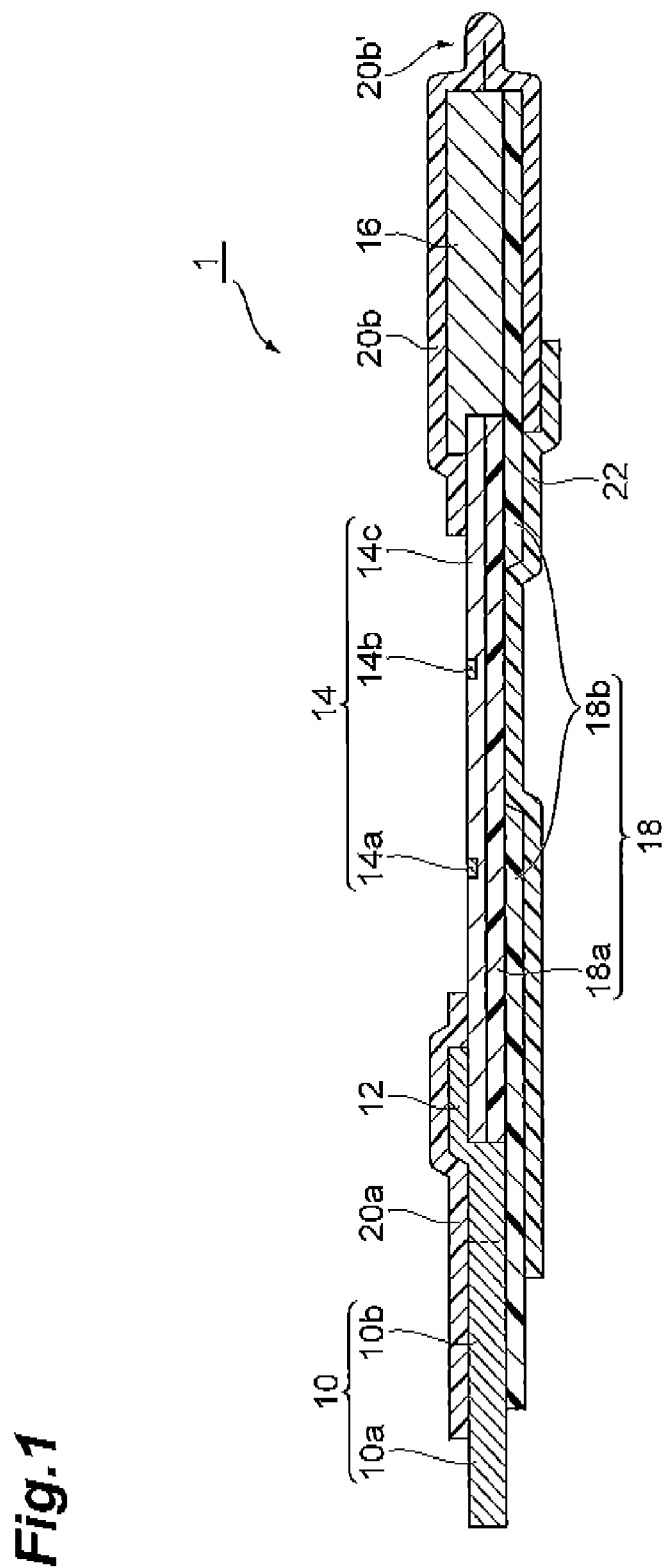
FIG. 1 is a lateral end view showing an embodiment of a detector according to the invention.

Hereinafter, the best embodiment of the invention will be described in detail, with reference to drawings as necessary. However, the invention is not limited to the following embodiment. In addition, in the drawings, the same elements will be marked with the same reference numerals, whereby repeated descriptions will be omitted. The dimensional ratio of the drawings is not limited to the ratio shown in the drawings.

FIG. 1 is a lateral end view showing an embodiment of the detector according to the invention. A detector 1 shown in FIG. 1 is for detecting IgE antibodies (analyte) in tears (liquid sample) of a human being. The detector 1 has a shape of a strip (a long and thin shape such as a band or a rectangle) with a width of about 1.5 mm and a length of about 57 mm, for example, and a mass thereof is about 0.032 g. The detector 1 includes a collecting member 10, a holding member 12, a detecting member 14, an absorbing member 16, a supporting member 18, a first adhesive member 20a, a second adhesive member 20b, and a background member 22. The collecting member 10, the holding member 12, the detecting member 14, and the absorbing member 16 are arranged on the supporting member 18 in the longitudinal direction of the detector 1, so that the tears move through the inside of these members in the above order of the members by capillarity.

The collecting member 10 is a member which is also called a "sample pad" and is used for absorbing and holding a liquid sample in the detector 1. Examples of the material of the collecting member 10 include filter paper, cotton, polyester, glass fiber, and the like. However, it is preferable that the collecting member 10 be an unwoven fabric including pulp.

The "pulp" refers to cellulose fiber extracted as a result of treating wood or other plants with a mechanical method and/or chemical method.

The "unwoven fabric" is a fabric obtained by superposing fibers in a constant direction or in random directions, without weaving or knitting the fiber, and shaping the resultant into a sheet. The unwoven fabric is different from a knit, paper, a film, and the like. Examples of a method of obtaining the unwoven fabric by making the superposed fiber into a sheet shape include a method of heating, a method of intertangling fibers, a method of using an adhesive, and the like.

The "filter paper" is paper used mainly for filtering and different from the unwoven fabric. The filter paper includes the one obtained from a raw material such as cotton fiber of fuzz (cotton linter) of seeds in the center of a cotton flower, and the one obtained from a raw material such as borosilicate glass fiber. However, the filter paper refers to any of those which is produced by being processed to obtain target characteristics (particle retentivity (μm), initial filtering rate, load capacity, ash content, and the like).

The unwoven fabric including pulp retains a large amount of water per unit mass, that is, has a high water retentivity. Accordingly, even when the amount of the analyte included in the liquid sample is minute, it is possible to improve the detection sensitivity by increasing the amount of the liquid sample collected. Moreover, being a soft material, the unwoven fabric including pulp does not easily cause pain when contacting the living organism and can reduce the burden imposed on the living organism when the liquid sample is directly collected from the living organism. In these respects, the unwoven fabric is also preferable.

It is difficult for the liquid sample to diffuse in the unwoven fabric including pulp. Accordingly, by using the unwoven fabric as the collecting member 10, it is possible to improve the separability of the analyte. Particularly, when the collecting member 10 and the holding member 12 share a single fibrous substrate, if the unwoven fabric including pulp in which liquid is not easily diffused is used as the fibrous substrate, there is an advantage that the labeling reagent held in the end portion of the downstream side of the fibrous substrate is held near the end portion without contacting the living organism when the liquid sample is directly collected from the living organism. Accordingly, the unwoven fabric including pulp is suitably used as the fibrous substrate in the detector 1 in which the collecting member 10 and the holding member 12 are integrated.

The pulp included in the collecting member 10 is preferably wood pulp having wood as a raw material since the pulp has high water retentivity, and preferably the one which is produced by a mechanical method of producing pulp by crushing wood with a physical force. Examples of the wood pulp include pulp having a needleleaf tree as a raw material, pulp having broadleaf tree as a raw material, and the like.

The content of the pulp included in the collecting member 10 is preferably 60% or more, more preferably 80% or more, and still more preferably 90% or more.

The collecting member 10 can be produced based on a known method. For example, the fiber of pulp is dispersed in the air by an, air-laid method to form mats, and the mats adhere to each other to form a sheet by means of a special binder, whereby the collecting member 10 that is the unwoven fabric including pulp can be produced.

Rayon and/or synthetic fiber may be further mixed with the unwoven fabric including pulp. By mixing these with the unwoven fabric, the strength, surface smoothness, and flexibility of the unwoven fabric improve. Particularly, the unwoven fabric mixed with the synthetic fiber is preferable in terms of an excellent water absorption rate.

The "rayon" refers to regenerated fiber which is produced in a manner in which the cellulose fiber such as pulp is dissolved in an alkali such as sodium hydroxide and carbon disulfide so as to be viscose, followed by spinning in an acid. The rayon is different from the synthetic fiber. The "synthetic fiber" is obtained in a manner in which synthetic polymers obtained by polymerizing low molecular weight monomers that are chemically synthesized using a raw material such as petroleum, natural gas, and the like are made into fiber through various spinning methods.

The unwoven fabric mixed with the rayon can be produced by laminating the rayon on both surfaces or one surface of the mat during the production of the mat. In addition, the unwoven fabric mixed with the synthetic fiber can be produced by mixing the synthetic fiber with an intermediate layer or a surface layer of the mat during the production of the mat.

It is preferable that the collecting member 10 be a compressed unwoven fabric. By using the compressed unwoven fabric, the speed of permeation and movement of the liquid sample in the detector 1 increases. Accordingly, the detection time is reduced, and the burden imposed on the living organism such as a patient with a dry eye syndrome is reduced. The density of the unwoven fabric is preferably 40 mg/cm$^3$ or more, and the thickness of the unwoven fabric is preferably 0.8 mm or less. The compressed unwoven fabric is obtained in a manner in which a normal unwoven fabric including pulp is compressed at a compression rate of 10% or higher until the thickness becomes 90% or less, for example.

The collecting member 10 includes a protruding portion 10a that sticks out of the supporting member 18 at the upstream side in the movement direction of tears (hereinafter, simply referred to as an "upstream side") and a non-protruding portion 10b that is a portion other than the protruding portion 10a. The protruding portion 10a is exposed without being covered with other members such as the supporting member 18, the first adhesive member 20a, and the like. The protruding portion 10a is shaped like a strip and includes a flat surface at the end portion thereof. The length of the protruding portion 10a is preferably 5 mm or more.

When the tears of a human being are collected using the detector 1, the protruding portion. 10a is inserted in the inferior conjunctival fornix of the subject, and tears are collected while the detector is hung in the vertical direction. At this time, since the protruding portion 10a is made with a fibrous substrate such as the unwoven pulp fabric, tears are easily absorbed. In addition, since the fibrous substrate is a material that is less irritating, even when the protruding portion 10a touches an eyeball, it is unlikely that the subject will feel pain, or the like. Moreover, it is easy to perform a series of procedures since the protruding portion 10a is shaped like a strip. Particularly, since the protruding portion 10a has a flat surface, and the surface contacts the sample collecting site, it is possible to further reduce pain of the subject. Furthermore, since the length of the protruding portion 10a is 5 mm or more, it is possible to prevent members other than the collecting member 10 from touching the eyeball and the like of the subject.

The tears absorbed in the collecting member 10 then move to the holding member 12 by capillarity. The holding member 12 includes the fibrous substrate of unwoven pulp fabric or the like and a labeling reagent binding specifically to IgE antibodies. The labeling reagent is obtained by labeling antibodies that recognize the IgE antibodies as antigens with gold colloid (labeling substance). The labeling reagent is held in the fibrous substrate in a state where the labeling reagent can move along with the movement of tears by being eluted in the tears. While moving along with the movement of the tears through the holding member 12 and the detecting member 14, the labeling reagent binds to the IgE antibodies in the tears and forms a complex of the IgE antibodies and the labeling reagent.

As the labeling substance, latex beads and the like can also be used in addition to the gold colloid. Here, it is preferable to use color-developing particles of red or blue that can be easily confirmed visually without requiring a special device for confirming labels.

In the detector 1 shown in FIG. 1, the holding member 12 shares a single fibrous substrate with the collecting member 10. The labeling reagent is held in the end portion of the downstream side of the fibrous substrate in the movement direction of the tears (hereinafter, simply referred to as a "downstream side"), whereby the holding member 12 is formed. In this manner, since the collecting member 10 and the holding member 12 are integrated, it is possible to improve the strength of the detector 1. In addition, since a single fibrous substrate is used, the liquid sample easily moves to the holding member 12 from the collecting member 10 by capillarity. When the collecting member 10 and the holding member 12 are not integrated, it is preferable to overlap both the members with each other to maintain the strength of the detector 1. However, if doing so, the total area, of both the members is prone to increase. In this respect, in the detector 1 shown, in FIG. 1, the integration can reduce the total area of both the members, and a volume permeated by the tears can be reduced. Therefore, it is possible to obtain sufficient detection results with, a smaller amount of the sample collected.

The fibrous substrate shared by the collecting member 10 and the holding member 12 includes a portion that is overlapped with a portion of the detecting member 14. The length along the longitudinal direction of the overlapped portion is preferably equal to or longer than the length along the longitudinal direction of the holding member 12 that is formed by holding the labeling reagent. That is, the length along the longitudinal direction of the overlapped portion is preferably equal to or longer than the length along the longitudinal direction of the portion in which the labeling reagent is held. In, the detector 1, the fibrous substrate is overlapped with the detecting member 14 so as to be the top. As a result, since capillary flow in a vertical direction is created in the overlapped portion, the liquid sample more easily moves to the detecting member 14 from the collecting member 10 and the holding member 12 by capillarity.

If the movement speed of the liquid sample moving to the detecting member increases, the measurement is completed in a short time even with a small amount of the liquid sample. Therefore, the burden imposed on the living organism such as the patient with a dry eye syndrome is reduced. In this respect, the length of the portion where the fibrous substrate and the detecting member 14 are overlapped with each other is more preferably longer than the length of a portion (holding member 12) holding the labeling reagent. On the other hand, if the length of the overlapped portion is long, there is an increase in restrictions in production, such as lengthening the liquid-impermeable supporting member, and immobilizing the overlapped portion with a longer adhesive tape to prevent peeling of the overlapped portion. In this respect, the length in the longitudinal direction of the portion where the fibrous substrate and the detecting member 14 are overlapped with each other is preferably 6 mm or less, and more preferably 5 mm or less. If the length of the overlapped portion is longer than 5 mm, the volume of a portion permeated by the tears increases, which leads to a tendency that it is difficult to collect a sufficient amount of tears for detection.

The detecting member 14 includes a nitrocellulose membrane 14c and the detection reagent and the control reagent that are immobilized to the membrane. The detection reagent is immobilized to a detection reagent immobilizing portion 14a on the nitrocellulose membrane 14c, in a linear shape orthogonal to the longitudinal direction of the detector 1. The detection reagent is an antibody that includes a recognition, site with respect to the IgE antibody and binds specifically to the IgE antibody. The detection reagent includes the recognition site that is different from that of the antibody included in the labeling reagent. By binding specifically to the IgE antibody, the detection reagent captures a complex of the IgE antibody and the labeling reagent. In this manner, when the detection reagent captures the complex, a line of a color (red when the gold colloid is used as the labeling substance, for example) originated from the labeling reagent appears in the detection reagent immobilizing portion 14a. It is possible to determine that the IgE antibody is present in the tears by visually confirming the line.

The control reagent is immobilized to a control reagent immobilizing portion 14b that is positioned at the downstream side from the detection, reagent immobilizing portion 14a on the nitrocellulose membrane 14c, in a linear shape orthogonal to the longitudinal direction. The control reagent is an antibody that recognizes the antibody included in the labeling reagent as an antigen. When the control reagent captures the labeling reagent in the tears moved thereto, a line of a color originated from the labeling substance appears in the control reagent immobilizing portion 14b, and the line is confirmed visually. In this manner, it is possible to determine that the tears have moved to the control reagent immobilizing portion 14b, that is, a sufficient amount of tears for detection have been collected.

The absorbing member 16 is made with a material such as cellulose that can absorb the tears. The absorbing member 16 absorbs the tears and the labeling reagent moving from the detecting member 14 by capillarity. After the collection of the tears, when the collecting member 10 is dipped in developing liquid such as purified water to develop the tears, the absorbing member 16 absorbs the developing liquid, whereby developing of the developing liquid is smoothly performed. That is, the absorbing member 16 has a function of preventing the reflux of the developing liquid. The absorbing member 16 also has a function of removing foreign substances rinsed with the developing liquid from the detecting member 14.

The supporting member 18 is made with a liquid-impermeable material such as PET, and includes a first supporter 18a and second supporter 18b. It is preferable that the length and width of the first supporter 18a be the same as that of the detecting member 14 and also serve as the lining of the detecting member 14. The first supporter 18a reinforces the structure of the detector 1, and prevents the detector 1 from twisting or bending while being operated. Since the first supporter 18a is made with a liquid-impermeable material, the tears in the detecting member 14 can, move through the detecting member 14 in the longitudinal direction without permeating the first supporter 18a.

The second supporter 18b is a transparent adhesive film made with PET and the like. However, the second supporter 18b may be a nontransparent adhesive film instead. The second supporter 18b is provided in the first supporter 18a side opposite from the detecting member 14. In the portion where the second supporter 18b is overlapped with the first supporter 18a, the second supporter 18b is preferably separated in a distance of about 5 mm in the longitudinal direction. It is preferable that the second supporter 18b extends 2 mm or longer toward the upstream side from the background member 22.

The second supporter 18b has an adhesive face to the first supporter 18a side, and adheres to the collecting member 10, the holding member 12 and the detecting member 14 as well as the detecting member 14 and the absorbing member 16, thereby reinforcing the detector 1. Since the second supporter 18b is made with a liquid-impermeable material, the tears in the collecting member 10 and the holding member 12 can move through the respective members in the longitudinal direction without permeating the second supporter 18b. Moreover, a case does not occur where the tears and the developing liquid permeate the second supporter 18b from the absorbing member 16, leak outside the detector 1, and contaminate the user's hand. In addition, since the second supporter 18b made with the liquid-impermeable material extends 2 mm or longer toward the upstream side from the background member 22, it is possible to prevent liquid from permeating the background member 22.

Since the second supporter 18b is separated in the longitudinal direction, it is possible to easily adjust the length of the detector 1 by changing the arrangement pattern of the second supporters 18b, whereby the variations of production are obtained. In addition, when the second supporter 18b is separated in a portion other than the portion where the second supporter 18b is overlapped with the first supporter 18a, the tears and the like are likely to leak outside the detector.

The first adhesive member 20a and the second adhesive member 20b are made with an adhesive paper tape, for example. The first adhesive member 20a includes an adhesive face. Through this adhesive face, the first adhesive member 20a adheres to the surface of the end portion of the downstream side of the collecting member 10 (that is, the non-protruding portion 10b), the holding member 12, and the end portion of the upstream side of the detecting member 14, which is a surface at the opposite side from the supporting member 18. The first adhesive member 20a includes a non-adhesive face at the opposite side from the adhesive face.

The first adhesive member 20a adheres to the collecting member 10, the holding member 12, and the detecting member 14. Accordingly, these members are prevented from being peeling off from each other, and the strength of the detector 1 improves. In addition, since the first adhesive member 20a covers the surface of these members, it is possible to prevent the tears from volatilizing from these members and to obtain sufficient detection results with a smaller amount of sample collected. The first adhesive member 20a covers these members as if pressing the members from the top, whereby the first adhesive member 20a promotes the movement of tears caused by capillarity. Furthermore, including the non-adhesive face at the outside of the detector 1, the first adhesive member 20a provides a holding portion (handle) for the user to hold the detector for use.

The second adhesive member 20b has an adhesive face, Through this adhesive face, the second adhesive member 20b adheres to the end portion at the downstream side of the detecting member 14, the absorbing member 16 and the end portion at the downstream side of the second supporter 18b as if covering these members from the downstream side. The second adhesive member 20b includes a non-adhesive face at the opposite side from the adhesive face and further includes a portion for pick up 20b' at the end portion of the downstream side. The portion for pick up 20b' is formed in a manner in which the second adhesive members 20b adhere to each other in a portion where the second adhesive member 20b is folded back.

The second adhesive member 20b adheres to the detecting member 14, the absorbing member 16, and the second supporter 18b. Accordingly, these members are prevented from being peeled off from each other, and the strength of the detector 1 improves. Particularly, the second adhesive member 20b adheres to these members as if covering these members from the downstream side. Therefore, the second adhesive member 20b can effectively reinforce the structure of the detector 1. Moreover, since the second adhesive member 20b covers the surface of the absorbing member 16 and includes the non-adhesive face at the outside, there is an advantage that the user who uses the detector 1 by holding the end portion of the downstream side of the detector 1 does not contaminate his or her hand. Particularly, when the user uses the detector 1 by holding the portion for pick up 20b', the user can more safely use the detector. That is, the second adhesive member 18b functions as a holding portion (handle) of the detector 1.

The background member 22 is provided, at the supporting member 18 side opposite from the detecting member 14. The background member 22 is a white paper tape (sealing paper for office use) having an adhesive face at the supporting member 18 side, for example. On the surface of the background member 22 side opposite from the supporting member 18, marks that indicate the positions of the detection reagent immobilizing portion 14a and the control reagent immobilizing portion 14b are added by coloring.

Since the white background member is provided, red developed upon capture by the gold colloid is highlighted. In addition, since the positions of the detection reagent immobilizing portion 14a and the control reagent immobilizing portion 14b are indicated, it is easy to confirm a red line in the respective position. Moreover, since the background member 22 has the adhesive face, the first supporter 18a and the second supporters 18b are adhered by the adhesive face, whereby the structure of the detector 1 is reinforced.

Here, when the background member 22 is made with paper, if liquid such as tears permeates the background member 22, it could be difficult to confirm the color development upon capture caused by the labeling reagent since the background rises or the detector twists, or sufficient detection results might not be obtained since the amount of tears moving through the detecting member 14 is reduced. In order to make it difficult for these states to occur, it is preferable that the first supporter 18a extend 2 mm or longer toward the upstream side from the background member 22.

The detector 1 can be produced in a production method including the following steps (1) to (7), for example.

(1) Holding the labeling reagent in the end portion of the sheet-shaped unwoven pulp fabric (formation of collecting member 10 and the holding member 12)

(2) Forming the nitrocellulose membrane 14c on the sheet-shaped PET (the first supporter 18a) by lamination (3) Linearly applying and immobilizing the detection reagent and the control reagent on the nitrocellulose membrane 14c (formation of the detecting member 14)

(4) Sticking the collecting member 10, the holding member 12 and the first supporter 18a together by using a transparent adhesive film (the second supporter 18b), and sticking the collecting member 10, the holding member 12, and the nitrocellulose membrane 14c together by using a paper adhesive tape (the first adhesive member 20a)

(5) Sticking the first supporter 18a and the absorbing member 16 made with cellulose together by using a transparent adhesive film (the second supporter 18b), and sticking the second supporters 18b, the absorbing member 16, and the nitrocellulose membrane 14c together by using an adhesive paper tape (the second adhesive member 20b)

(6) Sticking sealing paper for office use (background member 22) to the first supporter 18a, the second supporter 18b, and the second adhesive member 20b (7) Cutting a card of multi-layered structure formed in this manner into a slit shape with a width of 1.5 mm The invention is not limited to the above embodiments. The embodiments can, be appropriately modified as long as the modification does not depart from the scope of the invention.

Figure 2:
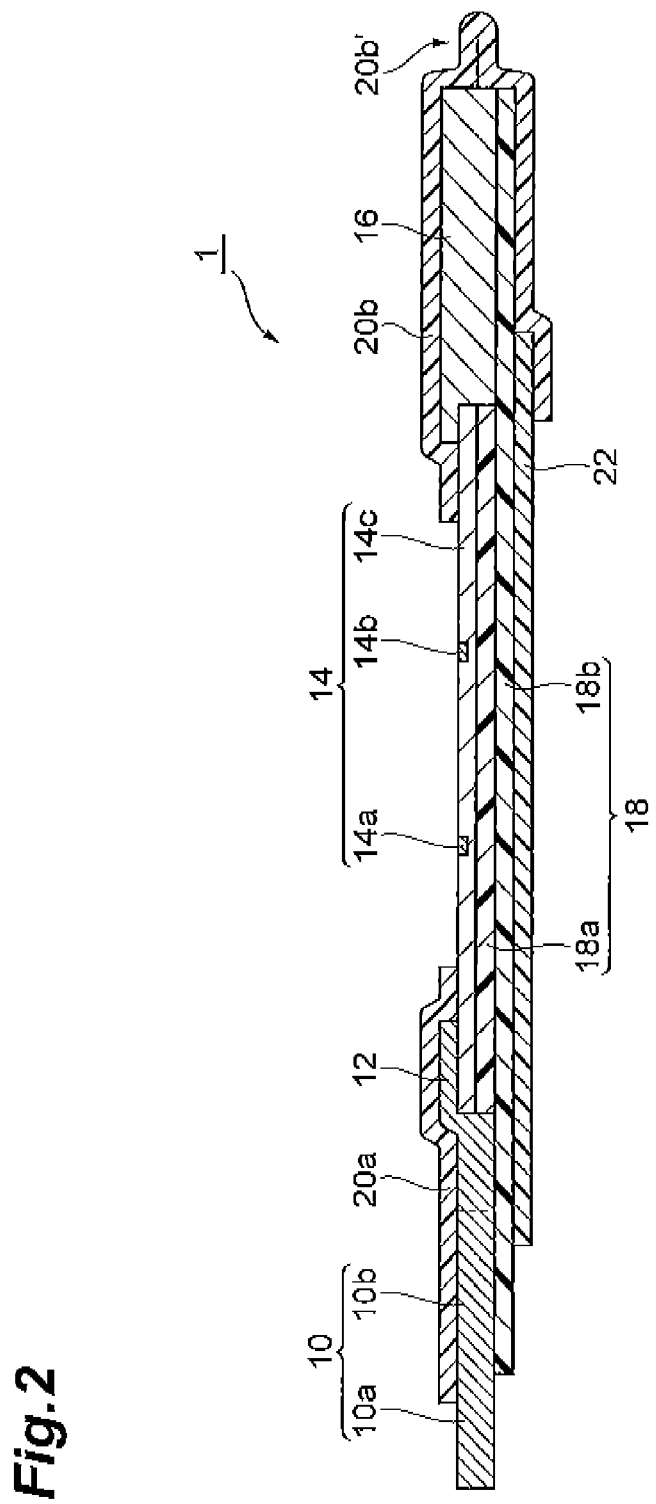
FIG. 2 is a lateral end view showing an embodiment of the detector according to the invention.

For example, as shown in FIG. 2, the second supporter 18b may not be separated. In this case, the length, of the detector 1 cannot be easily adjusted, but the structure of the detector 1 can be further reinforced. Moreover, as shown in FIG. 2, the second adhesive member 20b may adhere to the background member 22 through the adhesive face thereof. In this case, after the background member 22 is stuck to the second supporter 18b, the second adhesive member 20b is stuck to the background member 22.

Figure 3:
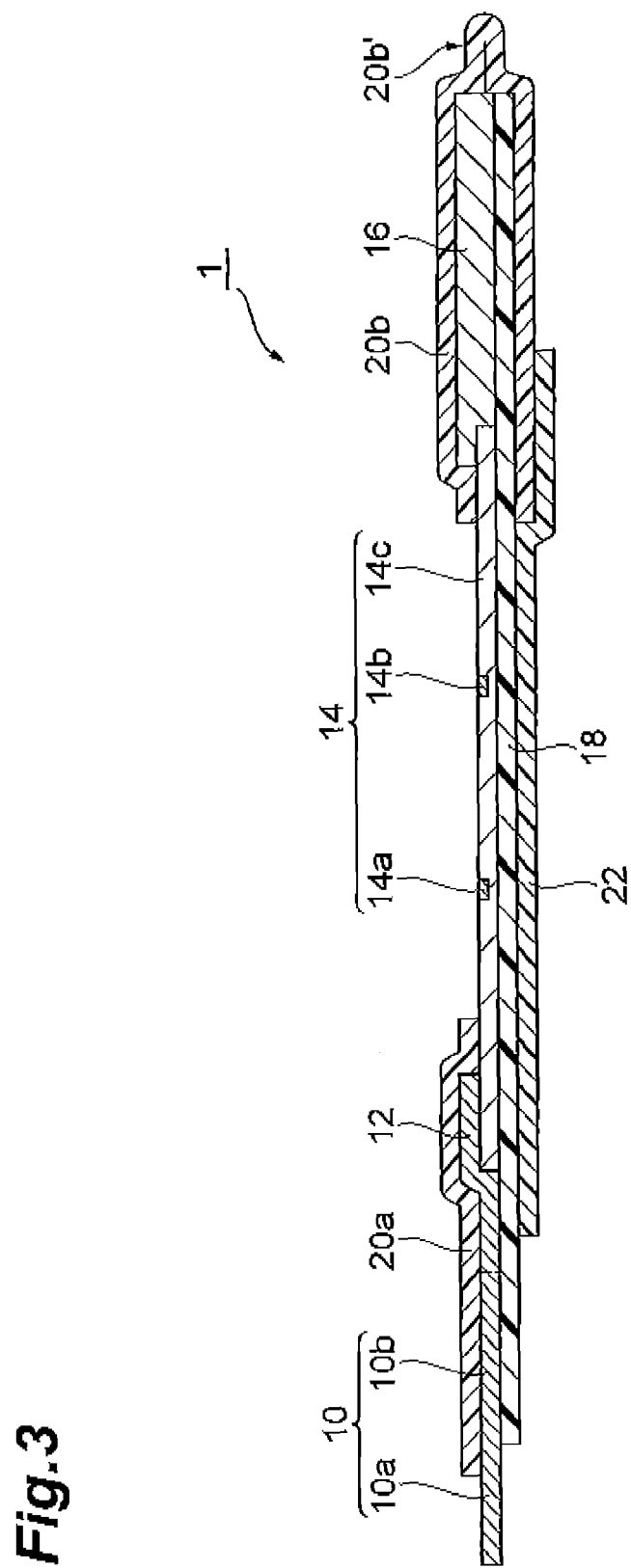
FIG. 3 is a lateral end view showing an embodiment of the detector according to the invention.
Figure 4:
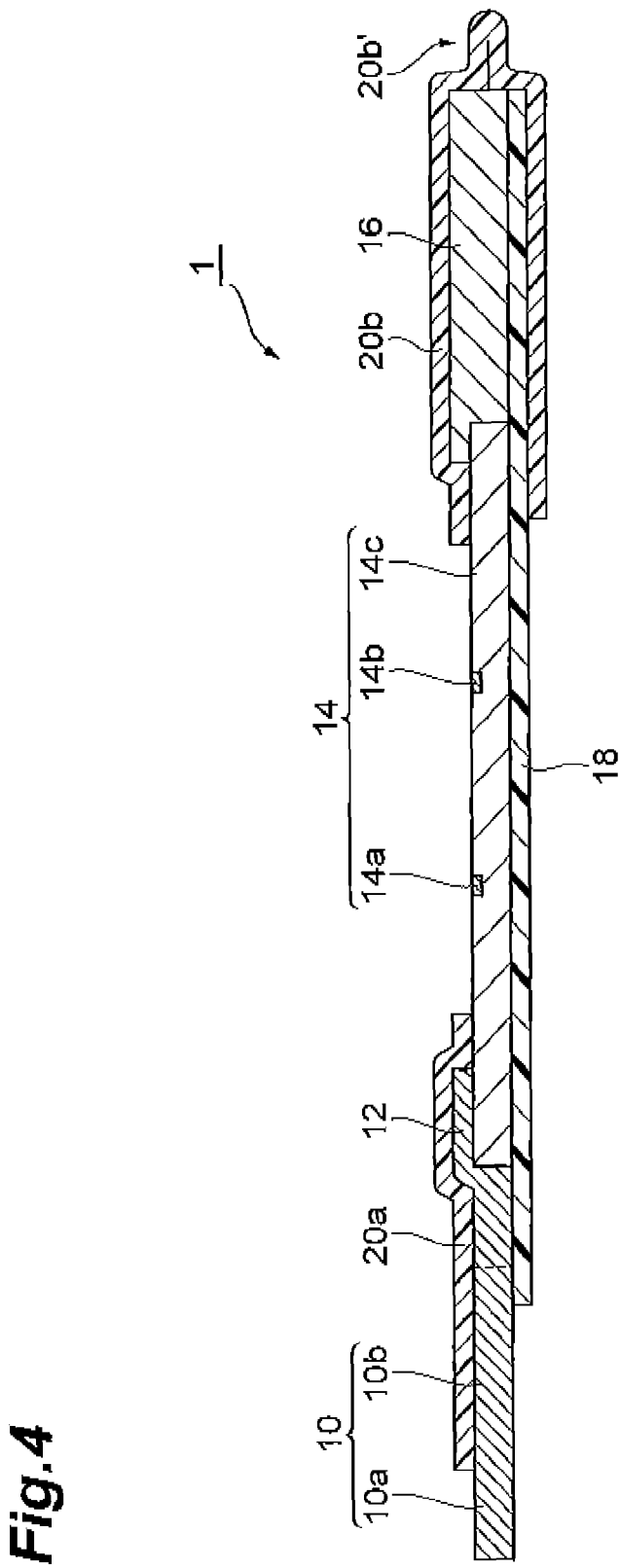
FIG. 4 is a lateral end view showing an embodiment of the detector according to the invention.

As shown in FIG. 3, the supporting member 18 may be integrally formed. Moreover, as shown in FIG. 4, the detector 1 may not include the background member 22. In this case, it is preferable that the supporting member 18 include a function of highlighting the color development upon capture caused by the labeling reagent. That is, it is preferable that the supporting member 18 is not transparent but has a color making it easy to visually confirm the color development upon capture, such as white.

Figure 5:
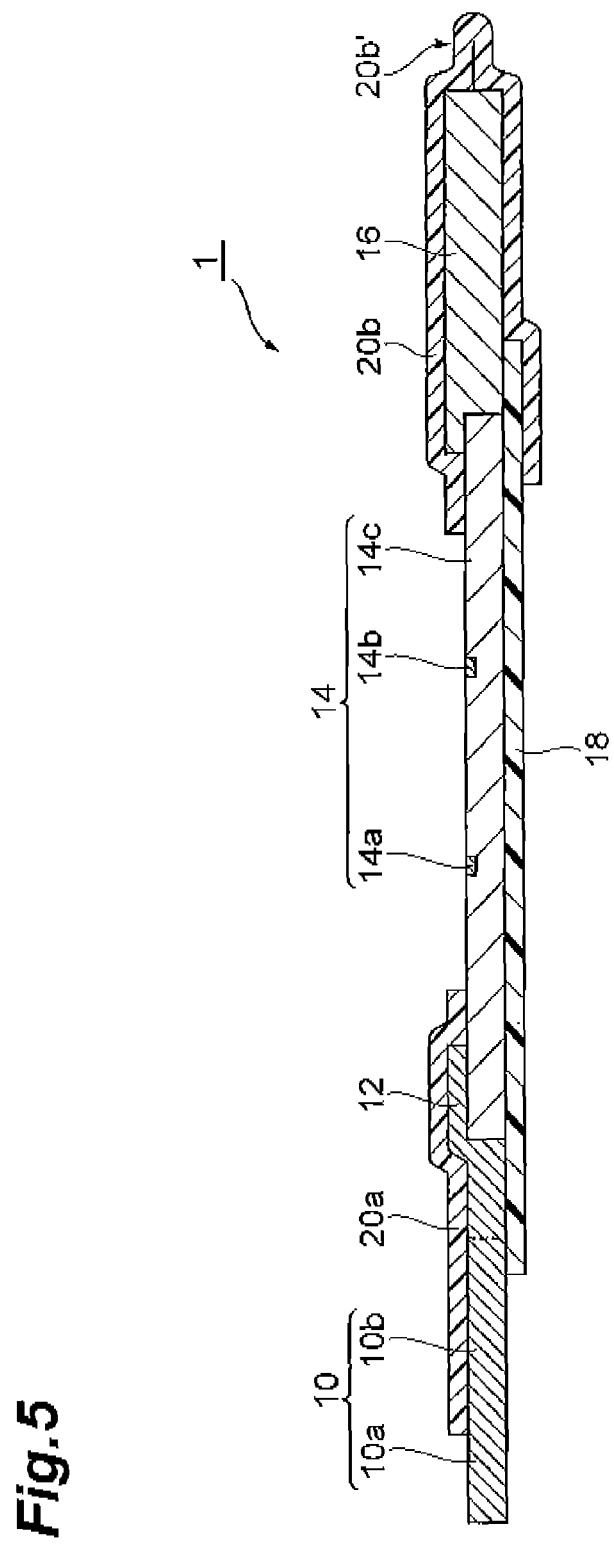
FIG. 5 is a lateral end view showing an embodiment of the detector according to the invention.
Figure 6:
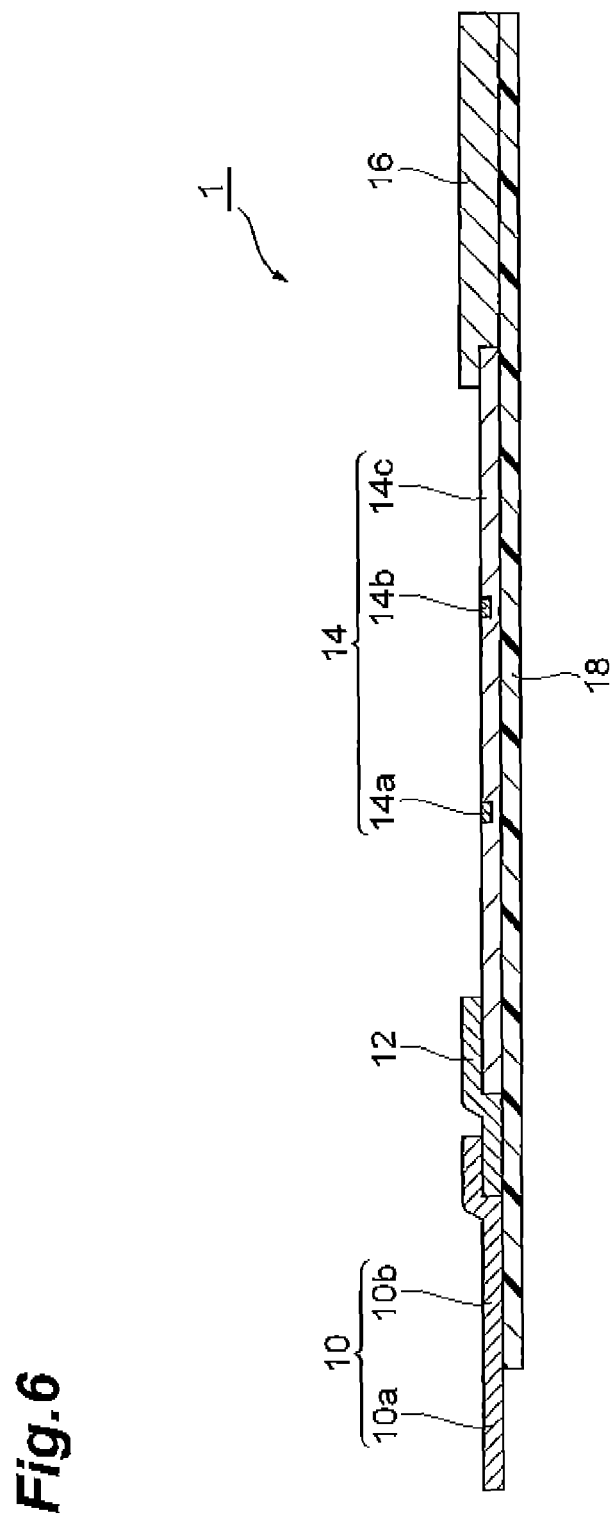
FIG. 6 is a lateral end view showing an embodiment of the detector according to the invention.

As shown in FIG. 5, the absorbing member 16 may extend toward the downstream side from the supporting member 18. Moreover, as shown in FIG. 6, the collecting member 10 and the holding member 12 may be formed of different fibrous substrates without being integrated. In this case, it is preferable that a portion of the collecting member 10 and a portion of the storage portion 12 be overlapped with each other. In this manner, the structure is reinforced, and the tears can easily move to the holding member 12 from the collecting member 10 by capillarity.

In addition, as shown in FIG. 6, the detector 1 may not include the first adhesive member 20a and the second adhesive member 20b. In this case, it is preferable that the supporting member 18 include an adhesive face and can stick the respective members together by using the adhesive face.

Example

Hereinafter, the invention, will be described in more detail by using examples. Here, the invention is not limited to the examples.

<Burden Imposed on Subject>

Tears were collected using the detector shown in FIG. 1. A detector was prepared in which the downstream side of a single fibrous substrate that the collecting member 10 and the holding member 12 share was overlapped with the upstream side of the detecting member 14 with a length of 1 mm, and an antibody solution ($OD_{520}$=8) labeled with gold colloid was applied in the end portion of the downstream side of the fibrous substrate in an amount of 22 µL/cm and with a length of 2.5 mm. When the subject suffers from a dry eye syndrome, since it took time (the time taken until tears come out) to collect a sufficient amount of tears for detection, it took 10 minutes or longer until a red line appeared in the control reagent immobilizing portion. However, it was possible to collect the tears without causing the subject to feel a burden. This result clearly showed that if the detector shown in FIG. 1 is used, it is possible to directly collect a sufficient amount of tears for detection from the subject without imposing a burden on the subject.

<Durability>

The detector was left for one month. As a result, the structure of the detector was maintained without twisting or bending. This result clearly showed that the detector shown in FIG. 1 has sufficient structural durability.

<Allowable Load>

A clip or the like was added to the detector to change the load, and the tears were collected. As a result, the detector to which the clip or the like was added fell from the inferior conjunctival fornix of the subject when the total load exceeded 0.8 g. This result clearly showed that the allowable load of the detector of the present example is 0.8 g or less.

<Water Retentivity of Fibrous Substrate>

The water retentivity of the following 8 types of fibrous substrates (A) to (H) was tested as follows.

(A) Kinocloth KS-40 (manufactured by OJI KINOCLOTH CO., LTD): unwoven wood pulp fabric (B) Palcloth P-40 (manufactured by OJI KINOCLOTH CO., LTD): rayon-mixed unwoven wood pulp fabric (C) Palcloth PB-40P (manufactured by OJI KINOCLOTH CO., LTD): rayon-mixed unwoven wood pulp fabric (D) Hi-cloth HAZ-40 (manufactured by OJI KINOCLOTH CO., LTD): synthetic fiber-mixed unwoven wood pulp fabric (E) Hi-cloth A-40 (manufactured by OJI KINOCLOTH CO., LTD): synthetic fiber-mixed unwoven wood pulp fabric (F) Whatman No. 41 filter paper (manufactured by Whatman Japan K.K): filter paper having cotton fiber as a raw material (G) Accuwick Ultra (manufactured by Pall corporation Japan): hydroxy polyester (H) S14 (manufactured by Whatman Japan K.K): glass fiber The respective fibrous substrates were cut into a 2 cm×2 cm square shape, and a mass (a) of the respective fibrous substrate pieces in a dry state was measured. The respective fibrous substrate pieces were put into a tray containing 15 mL, of ultrapure water, followed by shaking for 30 minutes while being sufficiently dipped into the ultrapure water, and then pulled up to a parafilm, whereby a mass (b) of the respective fibrous substrate pieces in a state of absorbing water was measured. The water retentivity (water retentivity I) was evaluated by the following formula.

(Water retentivity $I$)=$(b)/(a)$  (Formula)

After being shaken for 30 minutes while being dipped into the ultrapure water in the same manner as described above, the respective fibrous substrate pieces were pulled up to a metal sieve (32 meshes), followed by draining for 10 minutes, and then a mass (c) of the respective fibrous substrate pieces was measured. The water retentivity (water retentivity II) was evaluated by the following formula.

(Water retentivity $II$)=$(c)/(a)$  (Formula)

The results are shown in Table 1. In Table 1, "ND" means that the test was not performed.

TABLE 1

| Type of fibrous substrate | | Mass (mg) | | | Water retentivity I | Water retentivity II |
|---|---|---|---|---|---|---|
| | | (a) | (b) | (c) | (b)/(a) | (c)/(a) |
| (A) Unwoven wood pulp fabric | No mixing | 23.5 | 727 | 510 | 29.9 | 20.7 |
| (B) | Mixed with rayon | 22.6 | 541 | 438 | 22.9 | 18.4 |
| (C) | | 24.7 | 564 | 475 | 21.8 | 18.2 |
| (D) | Mixed with synthetic fiber | 18.8 | 433 | 317 | 22.0 | 15.9 |
| (E) | | 28.7 | 776 | 600 | 26.0 | 19.9 |
| (F) Filter paper | | 44.1 | 219 | 167 | 4.0 | 2.8 |
| (G) Hydroxy polyester | | 56.6 | 384 | 340 | 5.8 | 5.0 |
| (H) Glass fiber | | 34.1 | 390 | ND | 10.4 | ND |

As shown in Table 1, all of the unwoven wood pulp fabrics (A) to (E) showed relatively high values in the water retentivity I of 21.8 to 29.9 and the water retentivity II of 18.2 to 20.7. In contrast, all of the water retentivity I and the water retentivity II of the filter paper (F), the hydroxy polyester (G), and the glass fiber (H) showed relatively low values. These results clearly showed that the unwoven fabric having the wood pulp as a raw material had a higher water retentivity compared to the filter paper made from cotton fiber as a raw material, the hydroxy polyester, and the glass fiber.

<Labeling Reagent Holding Ability of Fibrous Substrate>

The labeling reagent holding ability of the 8 types of fibrous substrates (A) to (H) was evaluated based on the broadening (spot diameter) of a spot that was created when the antibody solution labeled with the gold colloid was dropped onto the substrates.

Specifically, to two locations separating from each other on the surface of the respective fibrous substrates, the antibody solution labeled with the gold colloid was dropped using a Pipetman by 5 μL, and the diameter (diameters 1 and 2) of each spot at a point of time when the broadening of the spot stopped completely was measured. As the antibody solution labeled with the gold colloid, a solution (particle size of 40 nm, manufactured by Tanaka Kikinzoku Kogyo) prepared in $OD_{520}=8$ was used. The labeling reagent holding ability was evaluated to be higher as the diameter of the spot decreases. The results are shown in Table 2 as shown in FIG. 9.

As shown in Table 2 of FIG. 9, the spot diameter in the unwoven wood pulp fabrics (A) to (E) was 3.5 mm to 4.0 mm, which was relatively small diameter. In contrast to this, the spot diameter in the filter paper (F) was 11.0 mm, which was a relatively large diameter. These results clearly showed that it is more difficult for liquid to diffuse in the unwoven fabric having the wood pulp as a raw material, compared to the filter paper having the cotton fiber as a raw material, and that the unwoven fabric having the wood pulp as a raw material has a high labeling reagent holding ability.

<Water Absorption Rate of Fibrous Substrate>

The water absorption rate of the 8 types of fibrous substrates (A) to (H) was tested based on a Byreck method which is a water absorption test method of fiber products.

First, the respective fibrous substrates were cut so as to prepare 3 pieces of fibrous substrate having a length of 6 cm and a width of 1.7 cm for each fibrous substrate, and a line was drawn with a marker in a position distant 0.5 cm from the end in the long-side direction. Thereafter, a tray containing water was prepared, and the respective fibrous substrate pieces were dipped into the water in the tray up to the line drawn with the marker. The upper end portion of the respective fibrous substrate pieces was fixed to the wall surface of the tray with a tape and left as it is for 3 minutes.

Figure 7:
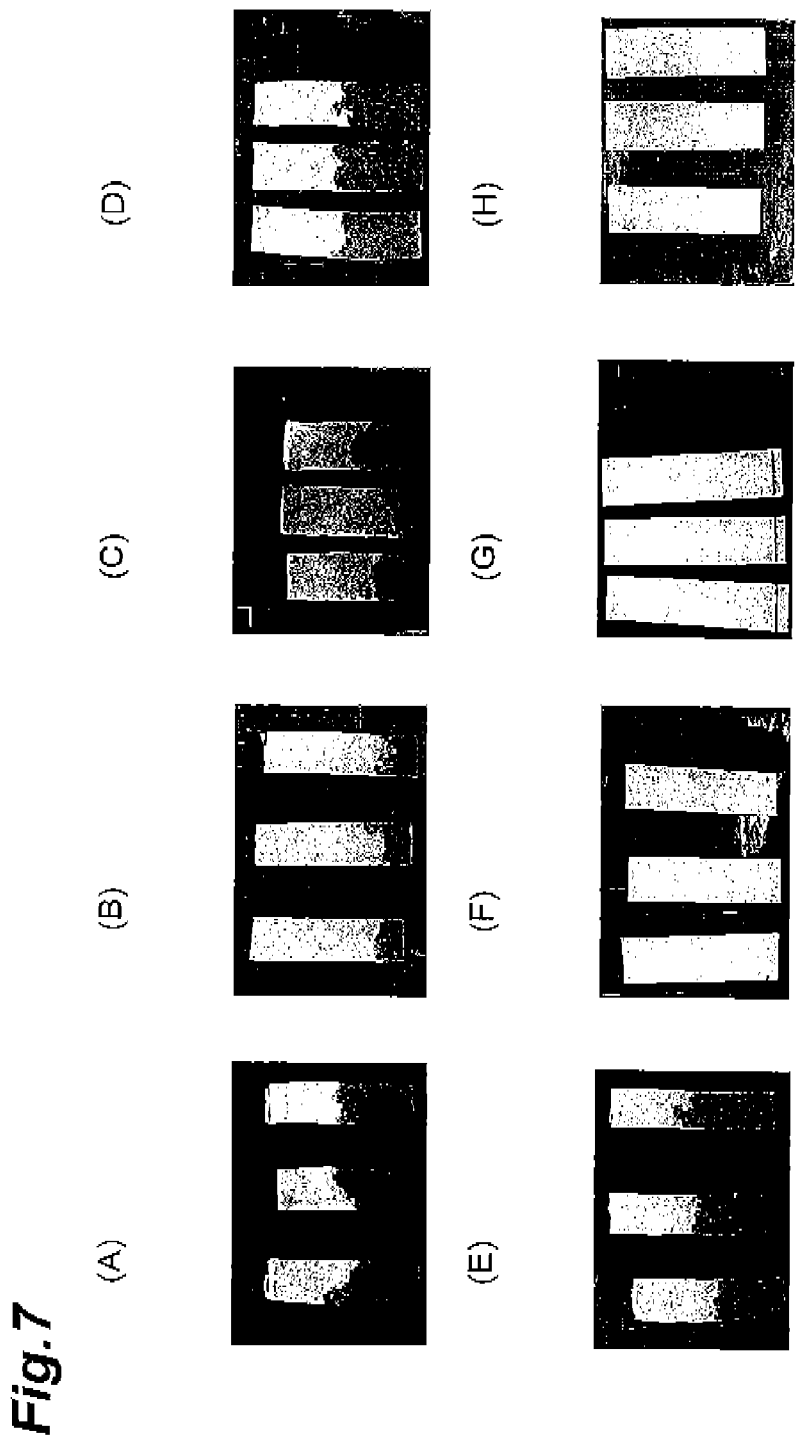
FIG. 7 is pictures showing results of water-absorbing rate test of each fibrous substrate.

Subsequently, the respective fibrous substrate pieces were taken out of the tray and placed on a parafilm, and a vertical distance (a maximum arrival distance) from the line drawn with the marker to a point where the water drawn up arrived at a highest point in a vertical direction, and a vertical distance (a minimum arrival distance) to a point where the water arrived at a lowest point were measured. The water absorption rate was evaluated to be higher as the maximum arrival distance increases. The results are shown in Table 3 and FIG. 7. In addition, the values shown in Table 3 are averages of the three fibrous substrate pieces.

TABLE 3

| Type of fibrous substrate | | Maximum arrival distance (mm) | Minimum arrival distance (mm) |
|---|---|---|---|
| (A) | Unwoven No mixing | 30.0 | 21.0 |
| (B) | wood Mixed with | 7.7 | 3.0 |
| (C) | pulp rayon | 11.0 | 6.0 |
| (D) | fabric Mixed with | 32.0 | 27.3 |
| (E) | synthetic fiber | 32.0 | 28.0 |
| (F) | Filter paper | 60 or more | — |
| (G) | Hydroxy polyester | 60 or more | — |
| (H) | Glass fiber | 60 or more | — |

As shown in Table 3, the water absorption rate of the synthetic fiber-mixed unwoven wood pulp fabrics (D) and (E) was obviously higher compared to the rayon-mixed unwoven wood pulp fabrics (B) and (C). In the filter paper (F), hydroxy polyester (G), and glass fiber (H), although accurate values could not be obtained since water was absorbed into the whole fibrous substrate piece, the water absorption rate was shown to be markedly higher compared to the unwoven wood pulp fabric.

Figure 8:
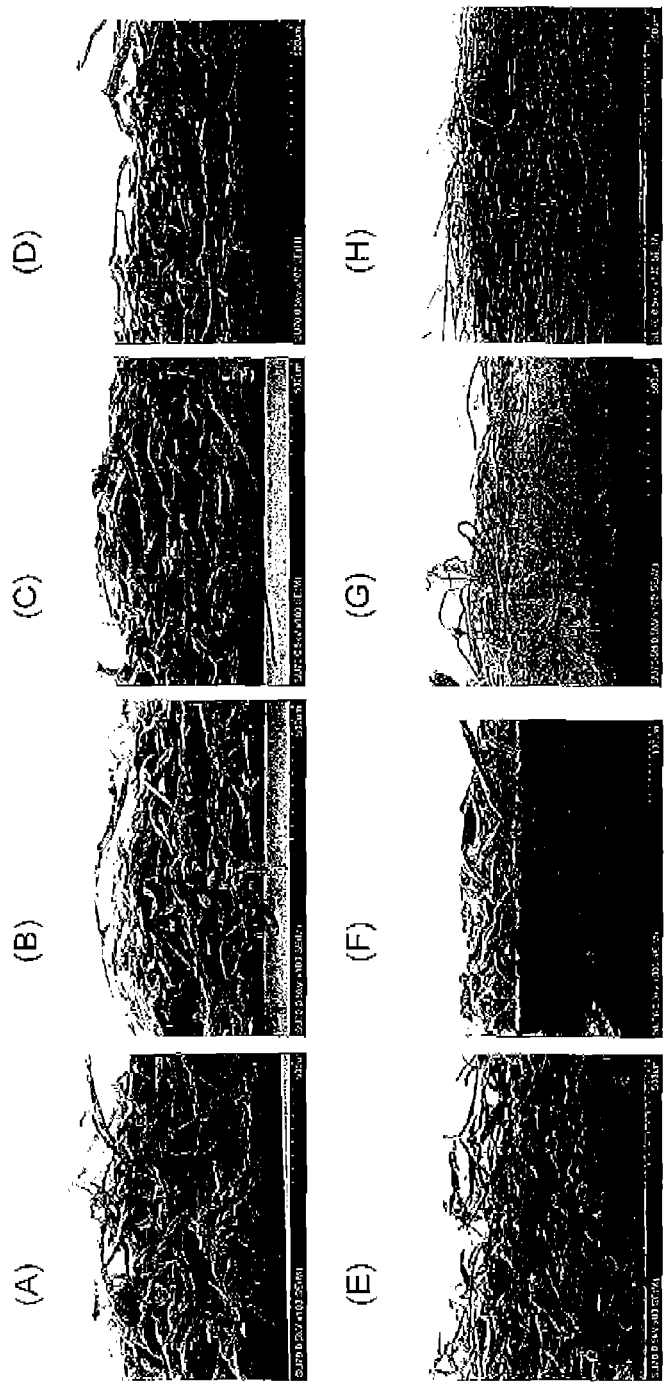
FIG. 8 is pictures of scanning electron microscope (SEM) of a cross-section of each fibrous substrate.

The structures of the fibrous substrates (A) to (H) were evaluated by taking pictures of cross-sections thereof with a scanning electron microscope (SEM). FIG. 8 is scanning electron, microscope (SEM) pictures of cross-sections of the fibrous substrates (A) to (H).

As shown in FIG. 8, all of the unwoven wood pulp fabrics (A) to (E) had a unique structure in which thick fibers were stacked on each other in layers while maintaining a space to some degree.

On the other hand, the filter paper (F) had a structure in which the fibers were compressed, and almost no space existed. The glass fiber (H) had a structure in which the very fine glass fibers were densely stacked on each other, and only a very small space existed.

The above results indicated that due to the structure in which the thick fibers were stacked on each other in layers while having a degree of space, which is unique to the unwoven wood pulp fabric, the diffusion of liquid is suppressed, and the amount of water retained per unit mass increases.

<Detection Time Reducing Effect>

(1) Detection Time Reducing Effect Caused by Compressed Fibrous Substrate

As the collecting member, detectors using one of the following two types of unwoven wood pulp fabrics were prepared respectively. To the respective detectors, an antibody solution ($OD_{520}=16$) labeled with the gold colloid was applied by 10 μL/cm as the labeling reagent.

"Kinocloth KS-40" (manufactured by all KINOCLOTH CO., LTD): thickness average of 1.03 mm (a minimum value of 0.85 to a maximum value of 1.15 mm), density of 39.3 mg/cm$^3$ "KS-40-pressed product": compression rate of 36.9%, thickness average of 0.65 mm (a minimum value of 0.5 to a maximum value of 0.75 mm), density of 58.9 mg/cm$^3$ Herein, the "thickness average" of the above two types of unwoven wood pulp fabrics is an average obtained in a manner in which an unwoven fabric having a width of 17 mm and a length of 25 cm is prepared, and the thickness at 10 arbitrary locations of the unwoven fabric is measured by a caliper. The minimum and maximum values of 10 times the measurements are disclosed in the parentheses.

The "compression rate" was calculated by the following calculation formula.

Compression rate (%)=100−(thickness average of "KS-40-pressed product"/thickness average of "Kinocloth KS-40")×100

To calculate the "density", the two types of unwoven wood pulp fabrics were cut into a 2 cm×2 cm square so as to prepare 3 sheets for each of the fabrics, an average mass (mg) per sheet in a dry state was determined, and the density was calculated by the following calculation formula from the average mass (mg) and the thickness average (cm).

Density (mg/cm$^3$)=average mass (mg)/[2(cm)×2(cm)×thickness average (cm)]

The following three types of samples were prepared as the liquid sample.
Sample 1: physiological saline (manufactured by OTSUKA PHARMACEUTICAL CO., LTD), total concentration of 0 (IU/mL)
Sample 2: total IgE concentration of 8.73 (IU/mL)
Sample 3: total IgE concentration of 34.05 (IU/mL)

By using the two types of detector respectively, detection was performed three times on 10 μL of the three types of the liquid samples having different total IgE concentrations, and a time (detection time) taken until a red line appeared in the control reagent immobilizing portion was measured. For the respective detectors, the average of the detection time was determined from nine times of the measurement in total. When the amount of the liquid sample was changed to 7.5 μL and 5 μL, the detection time was measured in the same manner, and the averages were determined. The results are shown in Table 4.

TABLE 4

| Amount of liquid sample (μL) | Average of detection time (sec) | | Detection time reduction rate (%) |
|---|---|---|---|
| | KS-40 | Pressed product | |
| 10 | 56.2 | 40.4 | 28.1 |
| 7.5 | 148.6 | 63.3 | 57.4 |
| 5 | 508 | 174 | 65.7 |
| Average detection time reduction rate (%) | | | 50.4 |

As shown in Table 4, compared to the detector using the uncompressed KS-40, the detector using the pressed product which was a compressed unwoven fabric reduced the detection time by 50% or more on average. Particularly, when the amount of the liquid sample was 5 μL, the detection time was reduced by 65.7%. These results clearly showed that the use of the compressed unwoven fabric as the collecting member and/or the holding member reduced the detection time and the burden on the living organism such as a patient with a dry eye syndrome.

Through visual observation, when a red line was not confirmed in the detection reagent immobilizing portion, it was determined as a class 0 (negative), when a line that was thinner than a line in the control reagent immobilizing portion was confirmed in the detection reagent immobilizing portion, it was determined as a class 1 (slightly positive), and when a line that was as thick as or thicker than a line in the control reagent immobilizing portion was confirmed in the detection reagent immobilizing portion, it was determined a class 2 (strongly positive). As a result, in all of the measurements, the sample 1 obtained a determination result of class 0 (negative), the sample 2 obtained a determination result of class 1 (slightly positive), and the sample 3 obtained a determination result of class 2 (strongly positive). In the detector using the pressed product that was the compressed unwoven fabric, it was confirmed that the detection time could be reduced without affecting the determination result, (2) Detection Time Reducing Effect Caused by Overlapping of Fibrous Substrate and Detecting Member 5 types of detector was prepared in which the downstream side of a single fibrous substrate that the collecting member 10 and the holding member 12 share is overlapped with the upstream side of the detecting member 14 in different lengths of 1 to 5 mm in the detector shown in FIG. 1 in which the collecting member 10 and the holding member 12 are integrated. As the fibrous substrate, "Kinocloth KS-40" (manufactured by OJI KINOCLOTH CO., LTD) was used, and an antibody solution ($OD_{520}$=8) labeled with the gold colloid was applied to the end portion of the downstream side of the fibrous substrate in an amount of 22 μL/cm. In this manner, a fibrous substrate in which the holding member 12 having a length of about 3 mm was formed in the end portion was used.

As the liquid sample, the following 3 types of samples were prepared.

Sample 1: physiological saline (manufactured by OTSUKA PHARMACEUTICAL CO., LTD), total IgE concentration of 0 (IU/mL)
Sample 2: total IgE concentration of 8.73 (IU/mL)
Sample 3: total IgE concentration of 34.05 (IU/mL)

By using the 5 types of detectors respectively, detection was performed three times on 10 μL of the three types of the liquid samples having different total IgE concentrations, and the time (detection time) taken until a red line appeared in the control reagent immobilizing portion was measured. For the respective detectors, the average of the detection, time was determined from nine times of the measurement in total. The results are shown in FIG. 5.

TABLE 5

| | Length of overlapped portion (mm) | | | | |
|---|---|---|---|---|---|
| | 1 | 2 | 3 | 4 | 5 |
| Detection time (sec) | 35.6 | 34.4 | 34.6 | 27.1 | 24.6 |

As shown in Table 5, when a detector was used in which the length of a portion where the fibrous substrate and the detecting member are overlapped with each other is longer than 3 mm which is the length of the holding member (a portion holding the labeling reagent), the detection time was reduced compared to the case of using a detector in which the length of the overlapped portion is shorter than 3 mm. This result clearly showed that by making the length of the portion where the fibrous substrate that includes the collecting member and the holding member and the detecting member were overlapped with each other longer than the length of the holding member which was a portion holding the labeling reagent, the detection time was reduced. This result led to an assumption, that the detection time might be reduced even when the amount of the liquid sample is smaller, and indicated that the burden imposed on the patient with a dry eye syndrome would be reduced.

Through visual observation, when a red line was not confirmed in the detection reagent immobilizing portion, it was determined as a class 0 (negative), when a line that was thinner than a line in the control reagent immobilizing portion was confirmed in the detection reagent immobilizing portion, it was determined as a class 1 (slightly positive), and when a line that was as thick as or thicker than a line in the control reagent immobilizing portion was confirmed in the detection reagent immobilizing portion, it was determined a class 2 (strongly positive). As a result, in all of the measurements, the sample 1 obtained a determination result of class 0 (negative), the sample 2 obtained a determination result of class 1 (slightly positive), and the sample 3 obtained a determination result of class 2 (strongly positive). It was confirmed that when the length of the portion where the fibrous substrate and the detecting member was 1 to 5 mm, the difference in the length did not affect the determination result, and when the detector in which the length of the overlapped portion was longer than 3 mm was used, the detection time could be reduced.

INDUSTRIAL APPLICABILITY

The detector and the detection method of the invention can be used for diagnosing an allergy such as pollenosis or the like by detecting IgE antibodies in the tears of a human being. The detector and the detection method of the invention can also use various types of liquid such as nasal secretions, the blood, wound exudate, and the like as the liquid sample, in addition to the tears. By detecting the antibodies and foreign substances included in the body fluid, the detector and the detection method of the invention can be used for diagnosing allergies and infection. In addition, particularly, by including a portion where the holding member and the detecting member are overlapped with each other in an appropriate length along the longitudinal direction, and by using the compressed unwoven fabric as the collecting member, the detector and the detection method of the invention can reduce the detection time. Accordingly, the detector and the detection method of the invention are suitably used for a patient with a dry eye syndrome for whom it is difficult to collect a sufficient amount of tears.

REFERENCE SIGNS LIST

1 . . . detector, 10 . . . collecting member, 10a . . . protruding portion, 10b . . . non-protruding portion, 12 . . . holding member, 14 . . . detecting member, 14a . . . detection reagent immobilizing portion, 14b . . . control reagent immobilizing portion, 14c . . . nitrocellulose membrane, 16 . . . absorbing member, 18 . . . supporting member, 18a . . . first supporter, 18b . . . second supporter, 20a . . . first adhesive member, 20b . . . second adhesive member, 20b' . . . portion for pick up, 22 . . . background member

The invention claimed is:

1. A strip-shaped detector detecting an analyte in a liquid sample, the detector comprising:
    a collecting member directly collecting the liquid sample from a living organism;
    a holding member including a labeling reagent binding specifically to the analyte, the labeling reagent being held in a state where the labeling reagent can move along with the movement of the liquid sample;
    a detecting member including a detection reagent capturing a complex of the analyte and the labeling reagent by binding specifically to the analyte, and the detection reagent being immobilized;
    an absorbing member being capable of absorbing the liquid sample;
    a liquid-impermeable supporting member, and
    an adhesive member,
    wherein the collecting member, the holding member, the detecting member, and the absorbing member are arranged in order on the liquid-impermeable supporting member in a longitudinal direction of the detector so that the liquid sample moves through the inside of these members in the above order of the members from an upstream side to a downstream side by capillarity,
    the collecting member includes a protruding portion sticking out of the liquid-impermeable supporting member at the upstream side in the movement direction of the liquid sample, and
    the adhesive member has: an adhesive face adhering to and covering an end portion of the downstream side of the detecting member, the absorbing member, and the end portion of the downstream side of the liquid-impermeable supporting member, a non-adhesive face at the opposite side from the adhesive face adhering to the respective members, and a pick-up portion provided at the end portion of the downstream side of the adhesive member configured to enable a user to hold the pick-up portion to pick up the strip-shaped detector, the pick-up portion comprising folded portions of the adhesive member folded such that adhesive faces in the folded portions adhere to each other.

2. The detector according to claim 1,
wherein the holding member includes a portion overlapped with a portion of the detecting member, and the length along the longitudinal direction of the overlapped portion is equal to or longer than the length along the longitudinal direction of a portion holding the labeling reagent in the holding member.

3. The detector according to claim 1,
wherein the collecting member and the holding member share a single fibrous substrate, and
the labeling reagent is held in the end portion of the downstream side in the movement direction of the fibrous substrate so as to form the holding member.

4. The detector according to claim 2,
wherein the length along the longitudinal direction of the overlapped portion is longer than the length along the longitudinal direction of the portion holding the labeling reagent in the holding member.

5. The detector according to claim 1,
wherein the collecting member is an unwoven fabric including pulp.

6. The detector according to claim 3,
wherein the fibrous substrate is the unwoven fabric including pulp.

7. The detector according to claim 5,
wherein the pulp is wood pulp.

8. The detector according to claim 5,
wherein the unwoven fabric is mixed with rayon.

9. The detector according to claim 5,
wherein the unwoven fabric is mixed with synthetic fiber.

10. The detector according to claim 5,
wherein the unwoven fabric is a compressed unwoven fabric.

11. The detector according to claim 10,
wherein the density of the unwoven fabric is 40 mg/cm$^3$ or more.

12. The detector according to claim 10,
wherein the thickness of the unwoven fabric is 0.8 mm or less.

13. The detector according to claim 10,
wherein the unwoven fabric is compressed at a compression rate of 10% or higher.

14. The detector according to claim 10,
wherein the density of the unwoven fabric is 45 mg/cm$^3$ or more.

15. The detector according to claim 10,
wherein the thickness of the unwoven fabric is 0.75 mm or less.

16. The detector according to claim 10,
wherein the unwoven fabric is compressed at a compression rate of 20% or higher.

17. The detector according to claim 1,
wherein the maximum width of the collecting member, the holding member, and the detecting member in a direction orthogonal to the longitudinal direction is 0.8 mm to 3 mm.

18. The detector according to claim 1,
wherein the detecting member further includes a control reagent binding specifically to the labeling reagent, and the control reagent is immobilized to the downstream side from the detection reagent.

19. The detector according to claim 1,
wherein the length of the protruding portion is 5 mm or more.

20. The detector according to claim 1, further comprising another adhesive member an adhesive face adhering to the surfaces of: the end portion of the downstream side of the collecting member; the holding member; and the end portion of the upstream side of the detecting member, the surfaces being at the opposite side of these members from the liquid-impermeable supporting member,
- wherein the another adhesive member includes a non-adhesive face at the opposite side from the adhesive face.

21. The detector according to claim 1,
- wherein the liquid-impermeable supporting member includes a first supporter also serving as a lining of the detecting member, and a second supporter provided on the opposite side of the first supporter from the detecting member.

22. The detector according to claim 21,
- wherein the second supporter is separated in the longitudinal direction in a portion where the second supporter is overlapped with the first supporter.

23. The detector according to claim 1,
- wherein the supporting member has a function of highlighting the color development upon capture caused by the labeling reagent.

24. The detector according to claim 1, further comprising a background member having a function of highlighting the color development upon capture caused by the labeling reagent, the background member being provided on the opposite side of the liquid-impermeable supporting member from the detecting member.

25. The detector according to claim 24,
- wherein the background member is a paper tape having an adhesive face on the opposite side of the liquid-impermeable supporting member from the detecting member, and
- the liquid-impermeable supporting member extends 2 mm or more toward the upstream side from the background member.

26. The detector according to claim 1, having a mass of 0.8 g or less.

27. The detector according to claim 1,
- wherein the living organism is a human being, and the liquid sample is tears.

28. The detector according to claim 1,
- wherein the analyte is an IgE antibody, the labeling reagent is an labeled antibody recognizing the IgE antibody as an antigen with a labeling substance, the detection reagent is an antibody recognizing the IgE antibody as an antigen and including a recognition site different from that of the antibody included in the labeling reagent, and the control reagent is an antibody recognizing the antibody included in the labeling reagent as an antigen.

29. A detection method of detecting an analyte in a liquid sample by using the detector according to claim 1.

* * * * *